United States Patent
Travish et al.

(10) Patent No.: US 10,893,838 B2
(45) Date of Patent: Jan. 19, 2021

(54) MEDICAL IMAGING SYSTEM HAVING AN ARRAY OF DISTRIBUTED X-RAY GENERATORS

(71) Applicant: Adaptix Ltd, Oxfordshire (GB)

(72) Inventors: Gil Travish, Oxford (GB); Paul Betteridge, Oxfordshire (GB); Mark Evans, Oxon (GB); Martin Holden, Wantage (GB); Abdul Sami Mughal, Oxford (GB); Kristin Schmiedehausen, Mountain View, CA (US)

(73) Assignee: Begbroke Science Park, CIE, Oxfordshire (GB)

(*) Notice: Subject to any disclaimer, the term of this patent is extended or adjusted under 35 U.S.C. 154(b) by 0 days.

(21) Appl. No.: 16/072,021

(22) PCT Filed: Jan. 25, 2016

(86) PCT No.: PCT/IB2016/000119
§ 371 (c)(1),
(2) Date: Jul. 23, 2018

(87) PCT Pub. No.: WO2017/130013
PCT Pub. Date: Aug. 3, 2017

(65) Prior Publication Data
US 2019/0029611 A1    Jan. 31, 2019

(51) Int. Cl.
*A61B 6/00* (2006.01)
*A61B 6/02* (2006.01)
(Continued)

(52) U.S. Cl.
CPC ............. *A61B 6/025* (2013.01); *A61B 6/06* (2013.01); *A61B 6/102* (2013.01); *A61B 6/107* (2013.01);
(Continued)

(58) Field of Classification Search
CPC .................................................. A61B 6/4007
See application file for complete search history.

(56) References Cited

U.S. PATENT DOCUMENTS

| 2009/0022264 A1* | 1/2009 | Zhou | A61B 6/025 |
|---|---|---|---|
| | | | 378/5 |
| 2010/0008465 A1* | 1/2010 | Matsuura | A61B 6/466 |
| | | | 378/62 |

FOREIGN PATENT DOCUMENTS

| JP | 2010505454 A | 2/2010 |
|---|---|---|
| JP | 2012522332 A | 9/2012 |

(Continued)

OTHER PUBLICATIONS

International Searching Authority, International Search Report, PCT/IB2016/000119, dated Nov. 8, 2016.
(Continued)

*Primary Examiner* — Dani Fox
(74) *Attorney, Agent, or Firm* — Reichel Stohry Dean LLP; Mark C. Reichel; Natalie J. Dean

(57) ABSTRACT

The disclosed system includes an emitter array for generating x-rays, a detector array for sensing a flux of x-rays transmitted through a region of interest; apparatus for holding, moving and aligning the emitter array relative to the region of interest and the detector array; electronic means for controlling the emitters and for reading and analyzing the output from the detectors and converting it to image data, and a display for displaying and manipulating the image data. The individual emitters are operated in multiple groups each illuminating a region of interest between the emitter array and the detector array such that the cone of radiation rays projected on the detector array from any single emitter in any one such group is substantially spatially separated from the corresponding projected cones from all other emitters in that same group.

3 Claims, 1 Drawing Sheet

(51) Int. Cl.
*A61B 6/10* (2006.01)
*A61B 6/06* (2006.01)

(52) U.S. Cl.
CPC .......... *A61B 6/4007* (2013.01); *A61B 6/4233* (2013.01); *A61B 6/4488* (2013.01); *A61B 6/482* (2013.01); *A61B 6/5205* (2013.01)

(56) References Cited

FOREIGN PATENT DOCUMENTS

| JP | 2014064705 A | 3/2014 |
| JP | 2014154499 A | 8/2014 |
| WO | 2009/012453 A1 | 1/2009 |
| WO | 2014/116665 A2 | 7/2014 |

OTHER PUBLICATIONS

International Searching Authority, Written Opinion of the International Searching Authority, PCT/IB2016/000119, dated Nov. 8, 2016.

\* cited by examiner

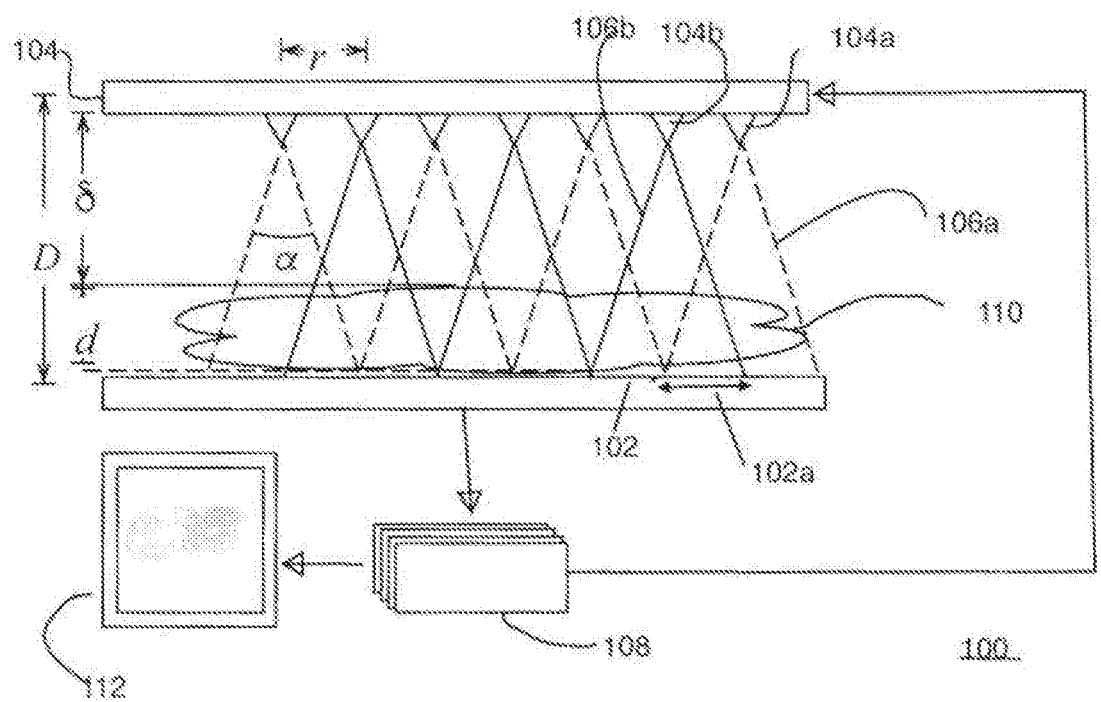

MEDICAL IMAGING SYSTEM HAVING AN ARRAY OF DISTRIBUTED X-RAY GENERATORS

PRIORITY

The present application is related to, and claims the priority benefit of, and is a 35 U.S.C. 371 national stage application of, International Patent Application Serial No. PCT/IB2016/000119, filed Jan. 25, 2016, the contents of which are hereby incorporated by reference in their entirety into this disclosure.

BACKGROUND

An x-ray imaging system may conceptually consist of:
1. A source used to generate x-rays;
2. A means of holding, moving and aligning the source;
3. An object to be imaged (i.e. the patient);
4. A detector for sensing the transmitted flux of x-rays;
5. A means of reading and analyzing the detector signals; and,
6. A means of displaying and manipulating the resulting image data.

Existing implementations of such a system, as is taught by past literature, have several shortcomings, including:
1. They are either unable to provide 3D information or require mechanical motion gantries to obtain the needed images;
2. They are either fixed and occupy a large space or, when mobile, weigh over 100 kg;
3. High capital costs to the end user (e.g. Hospital) and this often limits availability, especially for 3D systems such as CT; and/or
4. They lack the ability to selectively control radiation exposure required to acquire data from different regions of the object being imaged.

Healthcare Need

Planar 2D X-ray is the primary diagnostic imaging modality across the world, with in excess of 26 m examinations per annum in the UK alone (excluding dental imaging), and in excess of 300 m examinations in the US. Patients with inconclusive or suspicious findings are often referred for further evaluation for a high-cost 3D Computer Tomography (CT), a technology which has a relatively high radiation burden (1.5-8.0 mSv versus 0.1 mSv or less for planar x-ray) and is not as widely available as planar x-ray. In addition to a higher radiation exposure, this additional referral often increases the time to diagnosis and treatment as well as costs.

For diagnosis of lesions where tissues of radically different density are found Dual energy Radiology may be employed to discern between these tissues. In regular planar radiology this is only possible through exposure to fluxes of significantly different energy and processing the resulting data by subtracting/adding the image contrast in order to remove the soft or dense tissue from the image depending on the diagnosis desired.

Dose & Size Issues

Dose reduction is a significant driver in healthcare systems due to the increased use of imaging, in particular CT, and increased awareness of the risks of radiation. CT scans result in a large X-ray dose to the patient (typically circa 1.5 mSv for Low Dose CT (LDCT) and up to 8.0 mSv for full dose CT). In contrast to CT (360 degree scan), the 3D imaging technology of digital tomosynthesis (DT) images only a partial angle of a patient. Reducing excess dose is particular important for screening, as the patient is not known to be suffering a disease.

Conventional chest x-rays often show a pathology or abnormal finding of unclear significance. The radiologist reporting planar chest X-rays often identifies doubtful or equivocal findings that could be referred to as both pulmonary and extra-pulmonary lesions. In most of those cases the patients will be sent to a 3D CT scan for further evaluation In addition to additional waiting times and delays in patient management, a CT exam induces a relatively high radiation exposure and is expensive.

Currently available mobile 2D planar X-ray solutions typically weigh circa 200 kg (Philips Practix=175 kg, Siemens Mobilett=285 kg), have a large footprint and complicated setup. The weight of a source head alone demands an expensive and large mechanical arm for positioning and a need to shift hospital beds and remove support equipment from a patient's room in order to maneuver the device into position. The long stand-off distance required also limits the types of imaging that can be performed. Patients are disrupted for as much as thirty minutes and radiology technicians are occupied for up to an hour as they transport and position the large carts.

Source Issues

The conventional x-ray tube, a rotating anode device or simple Crooke's-tube-like configuration, is the workhorse of medical imaging systems. While countless refinements have been introduced, the basic mechanism remains the same. A high voltage supply is utilized to create an arc or discharge. Within the arc are electrons with kinetic energies at or near the applied potential. When these electrons strike a target (typically the anode), x-rays are produced through Bremsstrahlung ("Braking Radiation"). Conventional tubes can be relatively light (a few kg), but are typically fragile, being fabricated from glass. However, the power supplies are typically large, expensive and heavy (10s of kg). The majority of the applied power goes into waste heat, requiring cooling and further adding to bulk and weight.

Tubes represent the entrenched market leader with over 100 years of development history. These devices can be fragile, difficult to deploy in the field, and expensive. Maintenance of systems employing conventional x-ray tubes can be a substantial fraction of the initial capital cost per annum, and over the lifetime of the device dominate the total lifecycle cost.

Mini tubes may be small, but they still rely on expensive and bulky high voltage electronics required to drive system. They generally appear to have thermal management and burn out issues. There may also be issues in manufacturing large quantities of such devices.

Field Emitter Arrays (FEA)

Field emitters of electrons have been investigated in a number of contexts by a variety of researchers. In principle it is known that such field emitters, or arrays, of these emitters are able to produce x-rays by irradiating a bremsstrahlung target with electrons. The energy of the electrons, and hence of the x-rays emitted, is directly proportional to the applied voltage. Maintaining a sufficiently high voltage (30-120 kV) across a tiny gap without breakdown is very challenging and has been a barrier to miniaturization.

Radioactive Sources

Radioactive sources can also provide a good source of x-rays. Co-60-based-sources are still in use in developing countries for medical and dental x-rays. However, concerns about safety and nuclear material proliferation make these systems very undesirable. Moreover, such sources have no "off" switch and require shielding for safety implying that devices tend to be very heavy (10s to 100s of kg). This is not the direction of x-ray technology in the future.

Radioactive sources can be simple to operate, but have significant safety issues with handling, storage and disposal. Due to the shielding requirements, weight can also be an issue. The concerns with nuclear proliferation means that wherever possible, these sources are being replaced with "electronic" sources.

Carbon Nanotubes

Devices based on carbon nanotubes (CNT) allow for extreme field enhancement (the tubes are ~nm). A single emitter is unable to supply any significant level of current. By combining a large number of tubes per emitter, a modest current can be generated. However, the devices are fragile, difficult to fabricate, and still require external power supplies. The resulting devices are essentially microtubes, but with "cold cathodes".

CNT-based source offer, in principle, emitter ("Pixel" level) control. However, these sources require external HV supplies and the ability to accelerate the emitted electrons to final voltage.

Triboelectric Sources

Triboelectric phenomena have been known for many years. Triboluminescence (strain or fracture excitation) has also been recognized phenomena, and is familiar to anyone who has opened a glued package or chewed on a wintergreen lifesaver in the dark. Triboelectric based source can be very simple in design and construction. However, their performance appears to have a limited range of use and being mechanically based they appear to have issues with wear and maintenance of vacuum.

Conventional x-ray sources

X-ray tubes are fragile, usually being made of glass, have a short life, and have only limited suitability for situations outside a traditional hospital setting;

The power supplies needed to drive x-ray tubes are typically large, expensive and heavy (10s of kg);

The single point of emission requires that the x-ray source be placed a long and exact distance away from the patient. This "stand off" distance is demanded by both safety (due to skin exposure) and optics (due to the opening angle of the source);

This single point-source geometry demands complex thermal management and limits tube performance in many cases; and, The emission area is not selectable and the exposure can therefore not be shaped to include only the area of interest.

Currently two kinds of X-Ray PSUs are available. Integrated and non-integrated. Our invention comes under the category of the integrated type. The current state of the art in our area are integrated PSUs that are both big in volume as well as heavy in weight. They often require water cooling, and weigh around a 100 kg. This makes them, and hence the total product difficult to move, difficult to operate, as well as heavily dependent on usage area. Maintenance and operator usability is also difficult because of the bigger/heavier size of such power supplies.

Emission Control

Existing systems are based on an electrical or electronic means of controlling emission which uses either gating or gridding or a combination. Emission from field enhanced emitters can be switched off using current control (e.g. switches or transistors), or suppressed using intermediate voltage grids. Moreover, in a conventional x-ray tube with a thermionic emitter, switching off the emission involves controlling the high voltage supply pulse at about 100 kV or more with rise times around 1 milli-second or less.

Dual Energy

Existing dual-energy systems suffer from one or more problems including increased cost, increased workflow complexity, double dose to the patient and reduced image quality due to motion blur between subsequent energy exposures.

Reconstruction Approaches

Generating images from projections involves one or more of a number of approaches including stitching, tomography, tomosynthesis and other reconstruction methods. These methods constitute an entire field of study; here we simply indicate some approaches relevant to fixed-source three-dimensional image reconstruction and consider a few potential differences with existing image analysis approaches.

Medical Imaging Context

The two dimensional projection images used in medical radiography are based on differential attenuation of the applied radiation passing through a subject. Because biological subjects are transparent to x-rays of sufficiently high energy and intensity, the image captures information about all the tissues between the source and the detector.

2D radiographs are typically collected using point source to plane detector geometry, leading to substantial geometric distortion and parallax effects. They are typically presented as grayscale images, which require no special software support for visualization, although sophisticated systems are used for storage and management. They do require skilled human interpretation, not least because the overlapped information is converted into a medically meaningful representation by that interpretation. Human interpreters also use and expect to find familiar distortion and artifacts, and may tend to reject images which are too "correct".

The most developed three dimensional imaging technique is Computed Tomography (CT), which uses a moving source, collects many (essentially all) projections through the subject, and constructs usable image data by a direct algorithmic transformation of the collected data, described mathematically as applying the inverse Radon transform. CT scans collect much more data and involve higher overall doses than 2D radiographs; however they are susceptible to artifacts, particularly from relatively opaque materials.

2D Projections from 3D

Radiologists are accustomed to analyzing 2D images (projections). Thus, even with 3D capabilities, a distributed source must be able to generate 2D images. In addition, effect like parallax, despite being a "fault" in the image, may also be expected and desired by the human interpreters of medical imaging.

DRAWINGS

FIG. 1 shows the basic subsystems of an exemplary medical imaging system having a fixed array of x-ray detectors and a fixed array of x-ray emitters, and shows how adjacent emitters project overlapping beams of radiation on the same area of the detector array if operated simultaneously.

DETAILED DESCRIPTION OF THE INVENTION

As shown in FIG. 1, the invention concerns itself with x-ray imaging and specifically with medical imaging and radiology. The medical imaging system 100 described here consists of the following components:

1. A distributed planar source 104, used to generate x-rays 106;
2. An object 110 to be imaged, usually a patient or a body part of a patient;
3. A detector 102, used to measure the x-rays;
4. One or more computer workstations 108, 112, used to acquire the detector data, reconstruct the image and visualize the results, preferably by means of proprietary software; and
5. Hardware to mount and align the source and detector and position the patient.

Reference should now be made to FIG. 1, which shows the basic subsystems of an exemplary medical imaging system 100 having a fixed array of x-ray detectors 102 and a fixed array of x-ray emitters 104, in which adjacent emitters 104*a* 104*b* may project overlapping beams 106*a* 106*b* of radiation onto the same area 102*a* of the detector array 102 if operated simultaneously. As shown in FIG. 1, imaging system 100 also includes an acquisition workstation 108 which controls the radiation from the individual emitters 104*a* 104*b* (or groups of emitters) forming emitter array 104 and transforms the output data from the detector array 102 into a three dimensional array of data representing the radiation attenuation coefficient (i.e., the local density) at each point within an object being examined 110 (the "Region of Interest" or "ROI"). Visualization workstation 112 performs the calculations necessary to transform the image data from acquisition workstation 108 into one of more internal views of ROI 110 that are displayed to a radiologist or other medical professional.

As will be appreciated by those practiced in the arts the detailed design of these elements is driven by the medical imaging requirements and constrained by physics and practical engineering concerns. By way of example, the system described herein serves for medical imaging and may cover voltage ranges from 20-150 kV, exposure times from 10 msec-10 sec where the upper range of the exposure times are understood to include multiple frames, currents in the 1-10 mA range, and radiation fields from a few cm square to 43 cm×43 cm being typical. As can be appreciated by one practiced in the arts, other voltage, current and size ranges may be of interest.

In the above description of the invention, it is understood that subsystems and elements may be added or removed to accomplish specific imaging goals. The subsystems are understood to consist of a plurality of components.

In the disclosed invention, the source is a distributed array of x-ray generators. The source may consist of an array of emitters, an array of targets, a means of spacing the target from the emitters, a means of generating a high potential difference (voltage) across the emitter and target, a means of controlling emission from these emitters, a means of filtering the emission, a means of collimating the emission, and a housing.

System vs. Components

Systems designed and engineered for specific tasks consist, in general, of individual components. The system under consideration here is one of x-ray imaging, using a distributed array of x-ray sources, and comprising a detector to sense the x-rays after passage through an object to be imaged, and including a workstation and software to control the source, detector and reconstruct the image from a sequence of detector data sets.

The system is comprised of components, some of which may have been described in prior art. However, the prior art teaches away from the combination of these individual components in the way that this system teaches in the application and in such a way as to enable three dimensional imaging without movement of any of the components of the system, and in such a way that the dose requirements are low compared to prior approaches.

Additionally the system comprises an x-ray source which may be an array of field enhanced emitters driven by a high voltage source or pyroelectric crystal based field generator. Furthermore, the system comprises an x-ray source that may include a means of addressing individual elements of the source array such as electromagnetic coils which selectively activate production of x-rays from specific electron emitters while deactivating productions of x-rays from other emitters.

In the system disclosed, a detector may be comprised of a high-speed, low noise digital radiography sensor array. The system may contain a workstation for controlling the source and the detector. The workstation may further contain software to accomplish these control tasks. The scope of the invention in this system would not be limited to these specific examples, and components, and includes, as would be appreciated by those skilled in the art, many others.

Because the capabilities of the source and the nature of the x-rays produced are a strong determinant of the system design, details of the source are described next. Subsequent sections detail the other subsystems of the system disclosed here.

The Disclosed Source Technology

Prior art on x-ray generators generally teaches away from distributed sources and towards single point-like sources. Some prior art does teach towards distributed sources but using motorized gantries to move a single source across a pre-determined path. Very little prior art teaches towards the use of distributed sources which are based on fixed planar arrays of x-ray sources. These few existing articles of prior art differ in substantial ways from the invention disclosed here, and specifically:

Pitch: prior art teaches towards very high density arrays with source pitch well below 1 cm;
Control: prior art teaches towards control at the emitter through grids or switches on the emitter voltage input and away from target-based switching;
Array: prior art generally teaches towards emitters distributed in lines, arcs or a few rows and away from two-dimensional arrays;
Collimation: prior art generally teaches that each source should cover or substantially cover the entire object to be images, and teaches away from fractional coverage. The fractional coverage is fractional in both time and space.

The flat-panel array source disclosed herein preferably includes a fixed two-dimensional array; consisting of moderate pitch spacing in the mm to cm range; with emission control based on the generation of x-rays rather than the control of electrons; and, with collimation and stand-off distances that are designed to have the individual x-ray cones cover only a portion of the total area to be imaged. WO 2011/017645 A2 published on 10 Feb. 2011 and assigned to The Regents of the University of California discloses an exemplary field generator based on pyroelectric crystals such that cycling the temperature will induce the field that will drive the electrons to strike the bremsstrahlung target. One emitter consists of a pyroelectric crystal, bremsstrahlung target and collimator mounted on a substrate; the surface of the crystal is coated with a metal film). When the temperature of the crystal is cycled, spontaneous charge polarization occurs in the pyroelectric crystal, causing a perpendicular electric field to arise on its top and bottom faces. At the exposed crystal surface, this field is preferably enhanced by the ridges produced in micromachining, leading to field emission. The level of such field enhancement required is a function of the tip material and the applied field. For the cases of interest here, with fields in the 10-100 kV range over mm-cm gaps, the field enhancements are in the 100-1000 range, assuming metallic tips. These required levels of field enhancement are rather modest, especially when compared with plasma TV and carbon nanotube levels. Field emission is widely used in electron sources such as electron microscope guns, and is capable of producing the highest brightness beams. The field enhancement at the tip is proportional to the inverse of the tip radius. While a very sharp tip produces very large field enhancement, it reduces the maximum current that the tip can generate. Prior devices teach away from low enhancement factors and high voltages as disclosed here.

In some applications, it may be desirable to overcoat the emitter tips with a protective coating of Tungsten, Titanium-Nitride, Diamond-Like Carbon or other robust conductive material.

A high voltage power supply preferably powers the field emitter array and is packaged to provide a minimal height to preserve the flat-panel-like aspect ratio of the x-ray source.

The use of physically overlapping but essentially temporally separated cones of x-ray emission from individually addressed targets allows for seamless coverage of the object to be imaged (the "ROI"), maximal use of the available flux while maintaining the ability to have minimal stand-off distances.

A detailed description of exemplary design methodology particularly suitable for use with the present invention is disclosed and claimed in commonly assigned unpublished PCT application PCT/IB2015/057792 filed on 12 Oct. 2015 and entitled A METHOD OF DESIGNING AN X-RAY EMITTER PANEL. A copy of the Specification and Drawings of that application is attached hereto as Appendix A, and said application is hereby incorporated by reference in its entirety.

For additional details for a presently preferred process for recreating a 3-D image of the ROI, reference made be made to the commonly assigned patent application titled "Medical Imaging System with a Fixed Array of X-Ray Detectors and a Fixed Array of X-Ray Emitters for Producing a Digital 3-Dimensional Image" which is being concurrently filed herewith, a copy of which is appended hereto as Appendix B.

Thermal Considerations

In conventional x-ray sources, thermal problems often limit performance. Specifically, tight focal spots on the target are desirable for image resolution (i.e. point-like source), but cause high peak energy densities on the targets. Solutions such as rotating anodes and the use of refractory materials can increase the practical limits, but are expensive to implement. In addition to peak thermal limits, average thermal limits come from tube body and window heating and outgassing.

Unlike conventional sources, the thermal density of the disclosed x-ray source is quite low thanks to the large surface area. There are three thermal loads to consider: the power source (e.g. crystal energy input or high voltage generator waste heat); the emission tip (cathode) temperature; and, the target (anode) thermal load. In general, one can take energy densities of conventional tubes which are over a ~few $mm^2$ area and scale them by the 120,000 $mm^2$ of a full sized system.

Emission tip (cathode) temperatures are tolerated by fabricating the tips for materials that have a sufficiently high melting point. Different tip substrate materials may be combined with a variety of protective coatings, to provide a combination of robust thermal tolerance, good electrical conductivity, and emitter shape form factor, that together provide the requisite physical geometry and performance to generate field electron emission.

Target (anode) temperatures are controlled because the targets themselves are attached to a large thermally conductive surface area (i.e. the substrate). By distributing the target thermal load over a large area, allows the x-ray generation device to work as a solid-state component, thus avoiding the complications of thermal control required by conventional x-ray tube sources (e.g. rotating anodes, auxiliary coolant systems, etc.).

The power supply waste heat must be dealt with using conventional thermal control (e.g. fans), but again benefits from the large surface area of the flat panel source disclosed here.

Overall the system disclosed here further benefits from a reduction in the total power density from a reduction in the stand-off distance (source-to-detector) required thanks to the source array. As the radiation power required increases with the square of the stand-off distance (i.e. the "one over r-squared" law), the power required for the distributed source disclosed here can be substantially (e.g. one order of magnitude) below that of a conventional single point source.

Vacuum and Field Ionization

A presently preferred x-ray source employs electron beam generation by a set of field enhancing emitter (e.g. from a needle shaped tip). The electron beam is then directed at a transmissive bremsstrahlung target to produce x-rays. A vacuum is maintained between the cathode and anode for several reasons. First, the field produced by the needle is so immense that gas molecules near its +z or −z planes will become ionized. This ionization effect prevents the production of useful x-rays, or can produce ions that can damage the emitters and targets. Residual gas also causes the electron beam to scatter. Thus, vacuum needs to be maintained in the path between emitter and target.

The high vacuum conditions required for electron field emission to occur, are achieved during the manufacturing process, where the device is assembled under high vacuum. Once sealed, the trapped vacuum pressure is maintained at sufficiently low vacuum pressure throughout the operating lifetime of the device by the inclusion of an internal vacuum getter. The vacuum getter is coated onto an internal surface of the vacuum chamber, and/or a discrete getter component placed within or attached to the vacuum chamber during the manufacturing process. The vacuum getter is activated during the manufacturing process, and maintains the internal vacuum pressure of the device by chemically combining gas molecules, or by adsorption. The getter may also be re-activated periodically during the lifetime of the product, if necessary. Other mechanisms for maintaining vacuum are known such as mechanical and ion pumps.

X-ray Production:

Targets

In conventional X-ray sources the target is an anode held in the tube, either static or rotating such that when hit with electrons from the cathode it emits X-rays. Cooling the anode within a vacuum is difficult and can only use radiation to dissipate the heat.

The x-ray source disclosed here is connected the outer wall of each vacuum section, enabling a vast improvement in cooling of the source as the heat can be dissipated by conduction. These targets could be deposited on the inner surface of the vacuum chamber in the disclosed source in a variety of methods—thin film, sheet with conductive adhesive, MEMS processes or other. The use of a transmissive target as taught here, allows for configurations difficult to realize in the conventional reflective targets. Such targets could be deposited on a variety of suitable substrates such as silicon, glass or conducting materials, and could have a variety of geometries—a 'doughnut' shape, circular, or incorporating straight lines.

The most common target material used is tubes is tungsten. However, other materials such as molybdenum, rhenium, gold and other heavy metals and alloys thereof may also be used as target. A multilayer target design that offers different layer properties in different areas, with the characteristic of the X-Rays produced varying on the target the electrons hit, might also be suitable for certain applications.

Collimation

In conventional x-ray sources, a point to plane imaging geometry is used. The cone shaped distribution of radiation emanating from a single source can be idealized as a single point. This fan of photons traverses the body and is imaged on a flat plane. Ignoring intra-body scatter, the photons follow a straight line and their paths do not intersect. By contrast, in the x-ray source disclosed here, there are a multitude of sources. The overlap of one source with neighboring sources would cause blur due to the uncertainty of the photon source for a given detector region. A collimator or set of collimators can be used to limit the angle of emission for each emitter. One approach to this collimator is described in detail in commonly assigned International patent application WO 2015/132593 A1 published on 11 Sep. 2015 and entitled X-RAY COLLIMATOR. Another approach is to use a simple plate consisting of a dense material into which a set of holes of appropriate size have been made. A material such as tungsten or steel can be used to absorb the x-rays which fall outside the desired angle and hence outside the area of the holes for each emitter. These holes can be of various sizes. The collimator plate can also be made replaceable.

Field Generation

Field generation for use with field enhanced emitters (FEE) can use conventional power supplies or novel source of high fields. Prior art teaches that FEEs are to be driven by low- to moderate-voltage power supplies and generally teach away from the use of high voltages. Prior art also teaches away from compact power supplies where the gap between the ground and high tension plane is minimized.

A device for providing high voltage (e.g. −30 kV to −120 kV) to the emitters, such that the output plane of the power supply touches the emitter plane and provides an electrical contact. The device is geometry generally follows that of the emitter-target portion of the source. In one configuration, suitable for general radiology, a power supply of 30 mm thickness, and transverse size of 400 mm by 400 mm is considered. The device uses liquid and solid insulators to make such dimensions possible. The power supply is preferably part of the complete system, and will be part of the main enclosure.

Raster Control

The use of physically overlapping but temporally separated cones of x-ray emission from individually addressed targets allows for seamless coverage of the object to be imaged, maximal use of the available flux and, while maintaining the ability to have minimal stand-off distances.

As can be appreciated by one practiced in the art, the deflection of electron beams can be accomplished through several means and generally through electro-static, magneto-static and electro-magnetic means. These methods can be used to focus/defocus the beam as well as to deflect/steer the beam. Electrostatic methods include parallel-plate deflectors, as were commonly used in television tubes. Magnetostatic methods include solenoid coils and permanent magnets used to deflect or focus the electron current. Electromagnetic waves in combination with structures also can be used as beam optics.

By way of example, a magnetic field can be used to bend the beam out of the way. The advantage over the electrostatic deflector is that magnetic field can be produced away from emitter. Indeed, using edge fields, it is possible to produce a deflecting magnet at the target region. Coils placed above and below the target and emitter, respectively, can allow for a suitable deflecting field to be produced in the gap.

Commonly assigned International patent application WO 2015/132595 published on 11 Sep. 2015 and entitled X-RAY GENERATOR discloses a method of control which uses individually powered solenoids placed above each electron emitter and involves selectively either defocusing or deflecting the electron beam so that the majority of the particles do not strike a small transmissive bremsstrahlung target placed some distance in front of the particle source. The disclosed raster system works by energizing flat solenoids (coils) placed behind each emitter. When a coil is energized, the magnetic field deflects (and defocuses) the electron beamlet. The disclosed target (anode) layer is patterned so that only a small area has an effective bremsstrahlung material (e.g. tungsten) while the adjacent areas are low-Z material (e.g. Silicon) and the disclosed arrangement uses individually powered solenoids, requiring relatively high current coils. However, we have subsequently discovered that that clusters of such coils, when activated simultaneously, achieve similar results at lower currents.

To further maximize the available magnetic flux, in the region of the assembly where electrons are flying through free space, lensing is preferably utilized. Commonly used in electron microscopy, such lenses/yokes elongate the field in the beam axis direction and compact it in the off axis. There is a wide-range of flexibility in designing the raster coils, depending on applicable fabrication techniques, drive currents and voltages. A preferably preferred embodiment of such a coil uses layer-wound coils (wire), with an outer diameter of approximately 10 mm and an inner diameter of approximately 5 mm, with a design current of a few amps at 10 to 20 volts. Such a coil can potentially offer rise times below 1 ms and when configured in a cluster of coils around each emitter, a sufficient magnetic field would be generated capable of deflecting an electron beam in the 100 keV energy range traversing such a field by about 1 mm transversely. Such an electromagnetic coil windings is preferably arranged over a metal yoke, with the geometry of the yoke such that it will enhance the deflecting field while containing any stray fields.

The required speed of the raster coil+driver is a function of the desired image acquisition time and number of pixels in a raster area. A parallel scan is preferably performed over clusters of emitters in a tiled fashion. For instance, for a 30 cm×40 cm panel, raster areas of 10 cm×10 cm might be used, resulting in 12 "tiles". With a 1 cm nominal pitch, each tile contains some 100 emitters. For an image acquisition time below 100 ms, the required coil speed is less than 100 µs.

The coils preferably selectively deflect the electron beam over its short (typically ~1 cm) travel from the emitter (cathode) to the target (anode). A substantial deflection on the order of 1 mm will result in little to no background emission when "off" and will significantly reduce the burden on manufacturing tolerances.

Various combinations of coils can be exploited through the superposition of electromagnetic fields. In one particular such configuration, four coils surrounding a particular emitter-target set are used in combination to deflect the electron stream. In another configuration, eight coils are used: the inner four serve to produce a dipole deflecting field while the outer sets of coils serve to reduce the stray field from the inner coils and thus limit the effects on neighboring emitters. The coils may be driven in either polarity, which allows for a de-gauss stage during the firing sequence, which returns the previously magnetized steel yoke, to a state of repose.

The Detector

A hard x-ray detector is preferably incorporated which simultaneously provides three competing features: high resolution (<100 um pixels), large area (100s of cm2), and fast frame rates (e.g. >1 Hz at full resolution) from distributed sources with many (e.g. >10) emitters. T For fixed-source tomosynthesis and dual-energy imaging applications, two primary concerns arise over the detector specifications: speed and noise. The speed requirement is determined by the necessary frame rate to meet the maximal total exposure (image acquisition) time. Patient movement causes image blurring which typically limits exposure times to 100 ms and in almost all cases to less than 10s. Noise primarily comes from dark-current and from read-out noise. In single frame imaging, as long as the noise is well below the signal, the image quality can be considered high (in reality there is a more complicated dependence on contrast). However, in multi-frame imaging, the signal level can remain low for large parts of the image while the noise may add in quadrature. CMOS arrays are preferably utilized with the associated digitization circuitry (ADC) located at the column or even pixel level, which reduces or largely eliminates the low QE and poor SNR previously associated with such arrays.

Pixel size has a complex interplay with several parameters. CMOS arrays are commonly produced down to 2.3 µm pixels, however, this does not directly translate into the same resolution nor does it necessarily produce usable SNR. Scintillator coupling and segmentation must match the detector pixel size or blur can dominate. Smaller pixel size also implies low flux per pixel. The fill factor is also a primary concern. As pixel sizes shrink, it is necessary to eliminate any front side circuitry to maintain a high (near 100%) sensitive area. In medical imaging pitches vary from 30-150 µm with numbers above 100 µm being the most common.

Undesirable image lag can potentially result from charge carriers not being cleared (direct imaging) or scintillator decay (indirect imaging). However, commercially available detectors such CsI(TI) have a primary decay time of about 1 µs, and should not present a problem at a typical <10 KHz frame rate.

The Workstation

The workstation serves at least three functions:
1. Control of the source and detector settings;
2. Image acquisition; and,
3. Image processing (reconstruction).
   It may offer other features, such as but not limited to:
   Safety features, such as ability to disable emission in case of any error.
   Self-check, on a minimum of daily, or every time it is turned on, basis.

Depending on the processing demands, the reconstruction may require GPU accelerators or even shipping the data off to a cluster.

Image Processing

Image reconstruction is widely used in medical imaging, but is restricted to modalities such as CT, MRI and PET. Planar radiology has largely relied on human interpretation of direct images, even after the transition from film to digital detectors, with processing limited to visual improvements to assist interpretation.

Attempts have been made to use tomosynthesis as a means of extracting 3D information from sets of medical x-ray images for nearly 80 years. Until recently, these have not been practical, because of limitations in data gathering and image processing.

The available approaches for tomosynthesis are broadly:
shift and add—the conceptually simplest method of recombining images, which tries to produce the effect of bringing the detail in each layer of the scene in turn.
TACT (tuned aperture CT)—which uses fiducial markers introduced into the images to improve the effectiveness of shift and add
MITS (matrix inversion)—which attempts solve the reconstruction using linear algebra
Filtered backprojection—the basic technique used in computed tomography, which can be adapted to work with the limited angular range in tomosynthesis data sets
Algebraic reconstruction—in which an iterative solution is sought to a set of linear equations by minimizing some measurement of the "difference" between the observations and calculated values based on the current model
Statistical reconstruction—a superficially similar process to algebraic reconstruction based on determining a model with maximum likelihood All these techniques are combined in practice with a substantial amount of general image processing techniques—blurring, sharpening and filtering, applied both directly and to transformed data (Fourier space), preferably in combination with the sophisticated emitter panel design and image reconstruction process disclosed in the previously cited commonly assigned applications.

The Alignment Hardware & Housing

The housing for the system components disclosed here requires ruggedness as it has been proposed to be used in field medicine in combat and rural terrain. In general the source housing should be rugged, light, and versatile for multiple applications. The case materials must be compatible with medical device requirements such as sterility, alcohol wipe down, cytotoxcity etc. The housing must also have sensors for damage sensing and a means of indicating that the device has been subjected to too large an impact. Markings and other indicators not only need to meet various regulatory requirements, but should make for an obvious intuitive handling by the operator. In many applications, the source will be mounted on a frame or C-arm and will have to allow for connection to such a support system. Finally, the housing must support a mechanism for aligning the source to the detector through non-contact sensors and providing operator feedback through indicator lights or a video screen.

The basic requirements are therefore:
1. Provide a mechanically rigid platform for the x-ray source;
2. Aid in thermal control;
3. Protect the various subsystems from shock;
4. Shield the operator from backscattered radiation;
5. Allow for a sterile and cleanable work surface; and
6. Detect damage.

The detection of damage (mechanical shock, cracking, moisture, etc.) is a useful capability for such products. A preliminary assessment of the "self-shielding" of the device from backscattered/back-emitted radiation has been made and suggests that the inherent materials are sufficient to absorb the undesired radiation (e.g. no shielding materials are needed). In addition to the "self shielding" nature of the product, additional discrete backscatter shielding can be added where necessary.

Finally, there are external systems that are not integral to the housing but still of utility, including:

Recharge capabilities; (Can also be carried on-board if required).

Synchronization of the source and detector;

Remote control (push button or wireless); and,

A means for mounting the source and detector, and connecting the imaging workstation.

The presently contemplated embodiments of the present invention comprise various combinations of the various sub-systems mentioned above.

The emitters consist of a plurality of electron generators. In one embodiment the emitters are a plurality of field-enhanced emitters (FEE). In a further embodiment the emitters comprise a 2D array. In one embodiment, the array is regularly spaced forming a square grid. In another embodiment the array is on a triangular grid, sometimes referred to as a hexagon pack. In another embodiment the emitters are randomly spaced. The spacing and pattern of spacing are determined by the end-use, geometry of the imaging application, and factors such as desired resolution, as one practiced in the art would appreciate. The emitters may be fabricated from a variety of conducting materials including in one embodiment doped silicon. In another embodiment the emitters are made of Tungsten or Tungsten alloys. In another embodiment the emitters are made from highly conducting metals such as copper or aluminum. In a further embodiment the emitters are coated with a conducting film such as titanium nitride, tungsten, diamond, or other robust material.

The target consists of a plurality of metal films designed to convert the incident electrons into x-rays through Bremsstrahlung and other physical processes.

The target is supported on an electrically conducting substrate, which serves to complete the electrical circuit and to dissipate the heat energy deposited by the electron beam. •

The thickness of the target may be between 1 and 100 µm. The choice of target thickness depends on the atomic numbers of the target materials, their thermal properties, and the energy of the electron beam. A thickness of 10 µm of tungsten would be a typical value.

In one embodiment a small thin film of tungsten is supported by silicon. In another embodiment the target film is made of molybdenum. In another embodiment the target film is made of rhenium. In another embodiment the target film is made of gold. In another embodiment the target is made of other heavy metals. In a further embodiment the target is made of an alloy of two or more metals. In another embodiment the target consists of more than one layer of target materials. In a further embodiment two or more distinct target regions are placed in close proximity with the control mechanism used to select between them. In another embodiment the silicon substrate is replaced by another conducting material consisting of light elements, such as aluminum. In another embodiment the substrate is an insulating material with a conductive coating. In another embodiment, the target material is self-supporting.

The spacer between the emitters and targets serves to maintain a suitable separation and to insulate the cathode (emitter) from the anode (target). The thickness of the spacer is dependent on the materials used and the voltages applied. For example, smaller voltages mean less distance, and higher voltages may require high distances. The distance may vary, but may not be limited to, between 1 mm to 30 mm. In one embodiment the spacer is between 5 mm and 15 mm thick. In another embodiment the spacer is between 15 mm and 30 mm. In an embodiment of the invention the spacer is composed of glass. In another embodiment the spacer is borosilicate glass. In an embodiment of the invention the spacer is made of ceramic.

The field generator serves to produce a large potential difference (voltage) between the emitter (cathode) and target (anode). The field generator can be any means of producing the desired voltage. In one embodiment the field generator is a power supply which converts line voltage to a high voltage. The field generator will be able to produce, but may not be limited to, voltages up to 120 kV. In an embodiment of the invention the high voltage power supply is capable of producing between −20 and −120 kV. In another embodiment the power supply produces positive voltages. In an embodiment of the invention the system is packaged in a combination of liquid (insulating oils) and solid (putty, potting) to provide the insulation required for the high voltage field generator. In another embodiment, the power supply is connected to a battery. In another embodiment, the field generator is a plurality of ferroelectric crystals. In an embodiment of the invention, the field generator is capable of operating at two or more voltages either in parallel or sequentially. In an embodiment of the invention, the power supply operates at one fixed voltage. In a further embodiment of the invention the power supply operates at a fixed voltage in the range of 50-70 kV.

Emission control refers to one of many possible means of addressing or controlling the production of electron or x-ray emission from each emitter-target pair. It will be appreciated by one practiced in the art that these mechanisms of control are not limited to one approach and may be used in combination with one or more other methods. The underlying method of control is to deflect the electron beam from an emitter, individually, onto or away from the target to affect the production or cessation of x-rays, respectively. The amount of deflection required is a function of several aspects of the invention, as one practiced in the art will appreciate, and may depend specifically on the operating voltage, spacer distance, emitter pitch and target configuration. In the invention disclosed here, deflection ranges of 0.1 to 1.0 cm may be of particular utility, although it is understood that other ranges and values are of use.

In an embodiment of the invention the means of controlling the emission (of electrons) from the emitters comprises individually selectively powered solenoid coils placed above the emitter configured to selectively defocus or deflect the electron beam emanating from the emitter away from the target material thus preventing the generation of x-ray photons.

In a further embodiment, the individually selectively powered solenoid coils placed above the emitters are configured in clusters of coils, configured in a pattern essentially equivalent to that of emitter array. In one embodiment, these clusters consist of four coils arranged about each emitter, configured to create a dipole magnetic field. In another embodiment, the cluster consists of eight or more coils configured such that a central set of coils creates a dipole field for deflecting the beam trajectory of the emitter and surrounding coils are used to offset the stray field of the central coils, these clusters being configured in a pattern essentially equivalent to that of the emitter array.

In further embodiments of the invention solenoid coils are configured to enable the solenoid coil to switch in less than 1 milli second, and to deflect the electron beam a distance of 0.1 mm to 1.25 mm from the nominal path.

In further embodiments of the invention a yoke or set of yokes are used to shape the magnetic field produced by the coils so as to optimally impact the electron trajectory.

In an embodiment of the invention mechanical shutters are used to control emission of the x-ray. In a further embodiment electro-mechanical means are used to activate the shutters.

As can be understood by those familiar with the field, a means to selectively control the x-ray emission from the distributed array of x-ray generators will include electronic circuits. In an embodiment of the invention the means to selectively control the x-ray emission from the distributed array of x-ray generators comprises an electronic addressing and timing circuit configured to selectively activate one or more of the solenoid electromagnetic coils in a predetermined sequence. In another embodiment the means to selectively control the x-ray emission from the distributed array of x-ray generators comprises an electronic addressing and timing circuit configured to selectively activate one or more of the solenoid coils in order to mask the x-ray flux so that only a selected region of interest of the patient is exposed.

In an embodiment of the invention the targets and controls are arranged such that the system operates in the normally-on mode. In another embodiment, the targets and controls are arranged such that the system operates in the normally-off mode.

The filter in an x-ray source allows for the adjustment of the output spectrum and typically removes the low energy x-rays which are not beneficial for imaging and would otherwise deliver unnecessary dose to the patient. In one embodiment of the present invention, the filter consists of a plate of aluminum, typically a few millimeters thick. A variety of materials and configurations can be considered. As will be understood by one practiced in the art, filter selection is often related to "aluminum equivalent" thicknesses.

In an embodiment of the invention the means of filtering the x-ray photons generated comprises a sheet of aluminum of thickness 1 mm to 10 mm. In another embodiment, the filter consists of a copper sheet of thickness 1 mm to 5 mm, although other thickness find utility and are ultimately dependent on the operating voltage of the system and the specific end use. Other embodiments use a stack of alternating higher atomic number and lower atomic number materials, such as aluminum and carbon.

In an embodiment of the invention the filter is removable. In a further embodiment the filter is encoded such that control electronics cab read the specific filter in use.

The collimator serves to narrow the angle of x-rays emitted from the source. In a distributed source the collimator will be understood to be an array of individual collimators. In one embodiment the collimator consists of a plate of high density material with a plurality of holes designed to allow a plurality of x-ray cones to transmit with specific opening angles. In a further embodiment the collimator plate is composed of Tungsten, Steel, or an alloy of similar materials with high x-ray attenuation coefficients. In an embodiment of the invention the plate consists of Tungsten with a plurality aluminum inserts which serve to transmit a portion of the x-ray cones with well defined opening angles. In an embodiment of the invention the collimator consists of two plates, each plate containing a plurality of holes, the two plates arranged one atop the other such that a particular x-ray cone passes through a hole in first the lower and then the upper plate. In an embodiment of the invention the collimator consists of a plurality of tubes which serve to control the opening angle of the x-rays.

The detector serves to measure the x-rays. X-ray detectors typically consist of an array of sensors which either directly or indirectly (via a scintillator) measure the x-ray flux at each pixel. As will be appreciated by one practiced in the arts, several technologies can serve essentially the same function of capturing the x-ray flux and converting it to digital information. In an embodiment of the invention, the detector has a resolution (pixel size) between 30-150 µm. In a further embodiment, the detector uses CMOS sensors.

The computer workstation serves to acquire the data from the detector, process the data, reconstruct the image and render the image. As is known to those practiced in the art, more than one workstation can be used and in particular often the acquisition and imaging functions are separated into two workstations. As can further be appreciated, each of the aforementioned functions may use a cluster, grid or cloud of computers to accomplish the processing required.

The present invention preferably includes a means of visualizing, analyzing and storing the x-ray images acquired from the digital x-ray detector, which may include a computer workstation or laptop or other general purpose computing device. In other embodiments, the means of visualizing, analyzing and storing the x-ray images acquired from the digital x-ray detector comprises a mobile device such as a mobile phone or tablet device.

In some embodiments, the means of visualizing, analyzing and storing the x-ray images acquired from the digital x-ray detector comprises a computer workstation or other general purpose computing device with hardware acceleration such as Graphical Processing Units (GPUs) or Field Programmable Gate Arrays (FPGAs) configured to speed up the visualization and analysis of the x-ray images that are acquired. In another embodiment, the means of visualizing, analyzing and storing the x-ray images acquired from the digital x-ray detector further comprises remotely located computing resources such as cluster, grid or cloud computing resources. In other embodiments, the means of visualizing, analyzing and storing the x-ray images acquired from the digital x-ray detector further comprises telemetry based communication configured for the remote viewing of the x-ray images.

The software is used to carry out the functions prescribed above to the workstations. An imaging system requires several functions and therefore typically will have several conventional software components and libraries. However, the image reconstruction portion of the software varies in the approach used, depending on the hardware and desired end result. In one embodiment of the invention, the software uses spatially segmented tomosynthesis to reconstruct a 3D image from a series of 2D images. In another embodiment the reconstruction approach uses compressed sensing methods. In a further embodiment of the invention, a constrained refinement technique that minimizes the observed-calculated data distance subject to a sparsity constraint—favoring solutions that are compact and connected is employed.

The alignment and mounting hardware allows the source and detector to be positioned relative to the patient.

In one exemplary embodiment of the invention, the means for positioning and alignment of the array of distributed x-ray generators (relative to the digital x-ray detector and a patient positioned between the array of distributed x-ray generators and the digital x-ray detector) comprises a hinged mechanical support for the array of x-ray generators and a hinged support for the digital x-ray detector. Both hinged supports attached to a support frame, the base of the support frame comprising a roller and hinged and retractable horizontal stabilizers, such that in use the array of x-ray generators and the digital x-ray detector are supported in an aligned position by the hinges attached to the supported frame. The horizontal stabilizers are in the open position to provide the framework with stability and when not in use the array of generators and the digital x-ray detector can be folded against the frame, the horizontal stabilizers hinged away from the ground and the whole system may be moved by rolling the device using the roller attached to the base of the frame.

In another exemplary embodiment of the invention the means for positioning and alignment of the array of distributed x-ray generators and the detector consists of a fixed mechanical support.

In other embodiments of the invention the means for positioning and alignment of the array of distributed x-ray generators and the detector may include of a set of multi-jointed mechanical arms, and/or a c-arm which allows for the rotation and pivot of both the source and detector about the patient.

While only certain embodiments of the invention have been described and illustrated in detail herein, those of ordinary skill in the art will readily envision a variety of other means and/or structures for performing the functions and/or obtaining the results and/or one or more of the advantages described herein, and each of such variations or modifications is deemed to be within the scope of the present invention. More generally, those skilled in the art will readily appreciate that all parameters, dimensions, materials, and configurations described herein are meant to be exemplary and that the actual parameters, dimensions, materials, and configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and/or claimed. The present invention is directed to each individual feature, system, material and/or method described herein. In addition, any combination of two or more such features, systems, articles, materials and/or methods, if such features, systems, articles, materials and/or methods are not mutually inconsistent, is included within the scope of the present invention. Accordingly, the scope of the present invention is not intended to be limited to the exemplary embodiments described above, but only by the appended claims and such other claims (both new and amended) that may be added hereto prior to expiration of any rights based in whole or in part on this patent application. Moreover, such scope should not be interpreted as limited by the literal language of such claims, but rather is intended to include any obvious modifications or structural or functional equivalents thereto, both known and as yet unknown.

All definitions as used herein are solely for the purposes of this disclosure. These definitions should not necessarily be imputed to other commonly-owned patents and/or patent applications, whether related or unrelated to this disclosure. The definitions, as used herein, should be understood to control over dictionary definitions, definitions in documents incorporated by reference, and/or ordinary meanings of the defined terms.

The invention claimed is:

1. An x-ray imaging system comprising:
    a digital x-ray detector;
    a fixed two-dimensional array of distributed x-ray generators, configured with dimensions of at least 10×10 cm, and a pitch of approximately 1 cm, the fixed two-dimensional array of distributed x-ray generators comprising:
        a first group of non-adjacent first emitters configured to project non-overlapping beams of radiation onto the digital x-ray detector; and
        a second group of non-adjacent second emitters, each of the second emitters arranged to be adjacent to at least one of the first emitters, the second group of non-adjacent second emitters configured to project non-overlapping beams of radiation onto the digital x-ray detector;
        wherein each pair of adjacent second emitters and first emitters are configured to project overlapping beams of radiation onto a respective area of the digital x-ray detector, if operated simultaneously;
    a means to selectively control x-ray emission from the fixed two-dimensional array of distributed x-ray generators to temporally separate beams of radiation projected from each pair of adjacent second emitters and first emitters;
    a means to selectively control the x-ray emission from the fixed two-dimensional array of distributed x-ray generators,
    a means to control the acquisition of a plurality of x-ray image data obtained from the digital x-ray detector,
    a means of reconstructing the acquired data into a three-dimensional representation,
    a means of visualizing, analyzing and storing the x-ray images acquired from the digital x-ray detector,
    a means for positioning and alignment of the fixed two-dimensional array of distributed x-ray generators relative to the digital x-ray detector and a patient positioned between the fixed two-dimensional array of distributed x-ray generators and the digital x-ray detector.

2. An x-ray imaging system as in claim 1 whereby the fixed two-dimensional array of distributed x-ray generators comprise:
    a plurality of electron emitters;
    a plurality of targets;
    a means of producing a potential difference between the plurality of emitters and plurality of targets;
    a means of spacing the targets from the emitters;
    a means of controlling the emission of x-rays from each emitter-target pair;
    and a means of filtering the x-ray photons generated.

3. An x-ray imaging system as in claim 1 whereby the fixed two-dimensional array of distributed x-ray generators comprises:
    a planar array of distributed x-ray generators.

* * * * *